United States Patent
Tziviskos

[11] Patent Number: 6,151,526
[45] Date of Patent: Nov. 21, 2000

[54] RIBBED ELECTRODE FOR COCHLEAR STIMULATION

[75] Inventor: George Tziviskos, Woodland Hills, Calif.

[73] Assignee: Advanced Bionics Corporation, Sylmar, Calif.

[21] Appl. No.: 09/300,801

[22] Filed: Apr. 27, 1999

Related U.S. Application Data

[60] Provisional application No. 60/083,452, Apr. 29, 1998.

[51] Int. Cl.[7] ........................................ A61N 1/05
[52] U.S. Cl. .............................................. 607/137
[58] Field of Search ................... 607/116, 137; 600/373

[56] References Cited

U.S. PATENT DOCUMENTS

| | | | |
|---|---|---|---|
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 5,000,194 | 3/1991 | van den Honert et al. | 128/784 |
| 5,037,497 | 8/1991 | Stypulkowski | 156/245 |
| 5,443,493 | 8/1995 | Byers et al. | 607/137 |
| 5,545,219 | 8/1996 | Kuzma | 623/10 |
| 5,578,084 | 11/1996 | Kuzma et al. | 623/10 |
| 5,603,726 | 2/1997 | Schulman et al. | 607/57 |
| 5,645,585 | 7/1997 | Kuzma | 623/10 |
| 5,649,970 | 7/1997 | Loeb et al. | 607/57 |
| 5,653,742 | 8/1997 | Parker et al. | 607/137 |
| 5,667,514 | 9/1997 | Heller | 606/108 |

FOREIGN PATENT DOCUMENTS 9631087   3/1996   WIPO.

*Primary Examiner*—Scott M. Getzow
*Attorney, Agent, or Firm*—Bryant R. Gold

[57] ABSTRACT

An electrode array, made in a straight or curved shape, but made on a flexible carrier so that it can easily bend within a curved body cavity, such as the cochlea. The electrode array having a multiplicity of electrode contacts along a front side of the electrode array and a plurality of flexible ribs located on an opposite rear side. Insertion of the electrode array is performed by inserting the electrode array into the scala tympani (one of the channels of the cochlea) to a desired depth, which desired depth typically involves a rotation of about 360 degrees and causes the flexible ribs to make contact against the outer or lateral wall of the scala tympani, positioning the electrode contacts adjacent the inner wall of the scala tympani. To lock the electrode array in place, the electrode array is pulled back slightly, urging the flexible ribs into the outer wall thereby forcing the electrode array against the inner wall of the scala tympani, maintaining it in that position and preventing further removal of the electrode array. The electrode array is then attached to a tissue stimulation device.

15 Claims, 6 Drawing Sheets

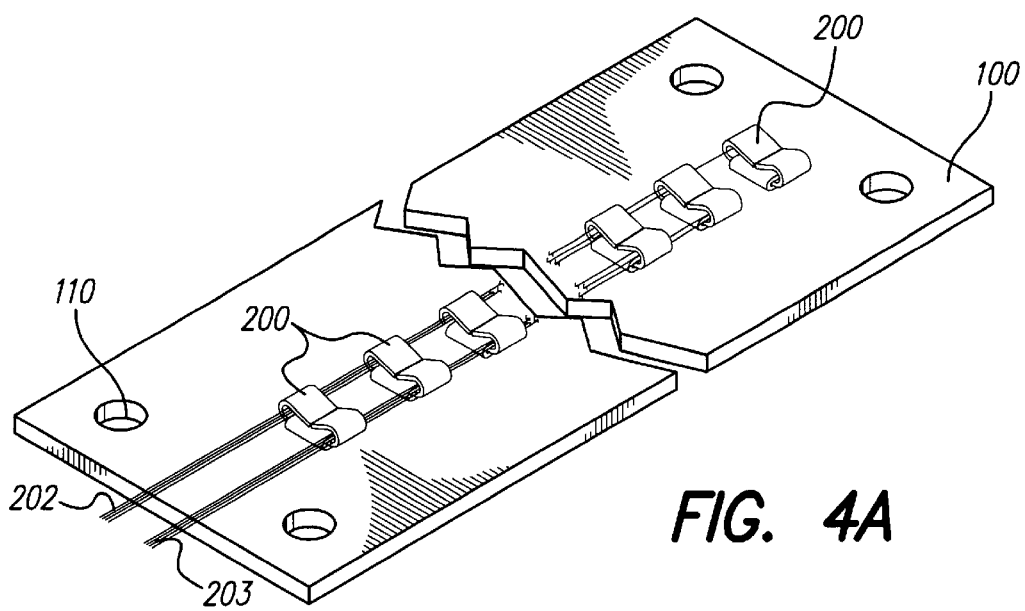
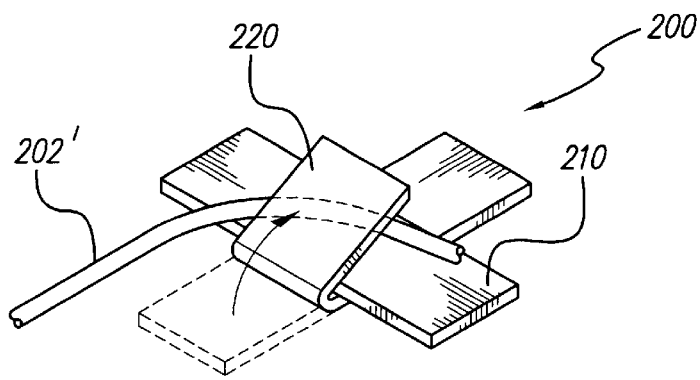
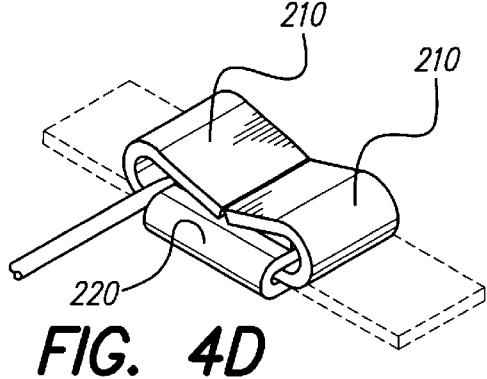 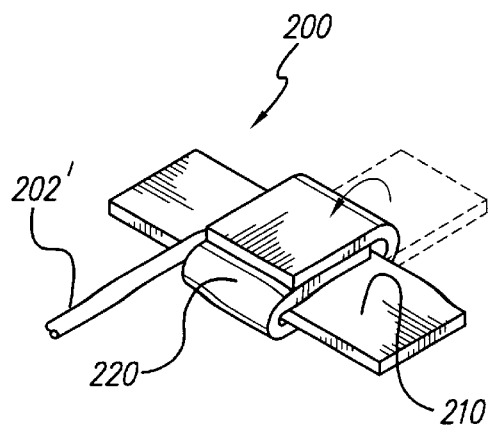
FIG. 4A
FIG. 4B
FIG. 4D  FIG. 4C

RIBBED ELECTRODE FOR COCHLEAR STIMULATION

This application claims the benefit of U.S. Provisional Patent Application Serial No. 60/083,452, filed Apr. 29, 1998.

BACKGROUND OF THE INVENTION

The present invention relates to implantable stimulation devices, e.g., cochlear prosthesis used to electrically stimulate the auditory nerve, and more particularly to a electrode for use with a cochlear stimulator that is designed with flexible ribs on the back of the electrode so as to place electrode contacts of the electrode array in close proximity to the ganglion cells and thereby to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems —or cochlear prosthesis— which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably contact the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani.

Thus, while it has generally been thought that enhanced performance of a cochlear implant could be achieved by proper placement of the electrode contacts close to the modiolar wall of the cochlea, two main problems have faced designers in attempting to achieve this goal. First, it is extremely difficult to assemble electrode contacts on the medial side of an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing an electrode system that allows for almost perfect positioning of the electrode contacts against the modiolar wall of the cochlea. Such "almost perfect" positioning is achieved through the use of an electrode system that includes an electrode array, preferably made in a straight shape, but made on a flexible carrier so that it can easily bend within the cochlea. The flexible carrier has flexible ribs located opposite the electrode array. The flexible ribs bias the electrode system inwardly in the cochlea so as to position the electrode contacts of the electrode array in close proximity to the modiolus wall.

Insertion of the electrode array is performed through the appropriate dimension of a cochleaostomy. This means the electrode array is inserted into the scala tympani (one of the channels of the cochlea) to the desired depth. The desired depth typically involves a rotation of about 360 degrees and causes the flexible ribs to engage the outer or lateral wall of the scala tympani. At this stage, the electrode is positioned very close to the modiolus of the cochlea. As a final optimization of the position of the electrode contacts of the electrode array, the electrode array is pulled back slightly (about 2 mm). This backward motion assures that the flexible ribs of the electrode array engage the lateral wall. Such engagement may further serve to force the electrodes into direct contact with the modiolar wall.

Advantageously, the electrode system of the present invention achieves the following goals: (1) it allows the electrode array to be optimally positioned against the modiolar wall in a cochlea; (2) it "locks" the electrode array in a desired position with flexible ribs; (3) it allows deep insertion beyond 360 degrees; and (4) it can be manufactured using easy, low cost technology.

BRIEF DESCRIPTION OF THE DRAWINGS

The above and other features and advantages of the present invention will be more apparent from the following more particular description thereof, presented in conjunction with the following drawings wherein:

FIGS. 4A, 4B, 4C and 4D illustrate one manner in which wires may be bonded to each of the electrode contacts of FIG. 3B during manufacture of the electrode array;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches one type of electrode system that may be used with a cochlear stimulation system. Other electrodes and electrode systems may also be used for this purpose as disclosed, e.g., in previously-filed, commonly-owned, patent applications Ser. No. 09/140,033, filed Aug. 26, 1998, Ser. No. 09/140,034, filed Aug. 26, 1998 and Ser. No. 09/140,035, filed Aug. 26, 1998, incorporated herein by reference. The materials, dimensions, methods of manufacture, and the like, described in these prior-filed patent applications are also applicable to the present invention.

Figure 1A:
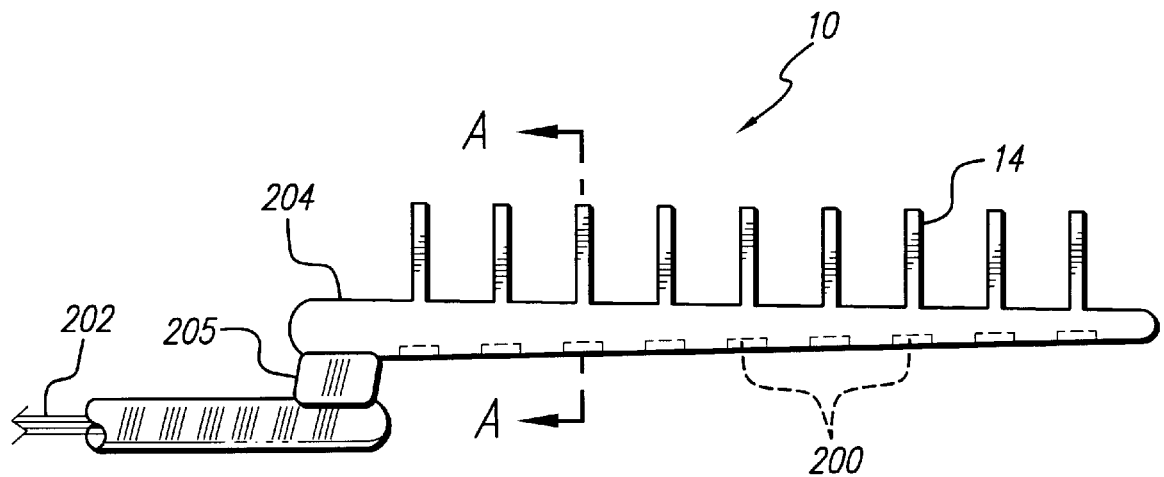
FIGS. 1A and 1B show a side and cross-sectional view, respectively, of an electrode array which forms of the present invention.
Figure 1B:
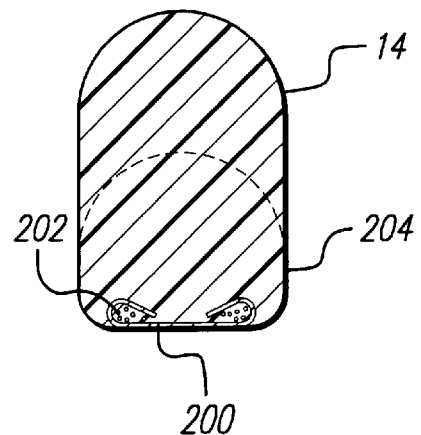

Turning to FIGS. 1A and 1B, there is shown a side and a cross-sectional view, respectively, of an electrode array 10 made in accordance with the present invention. The cross-sectional view of FIG. 1B is taken along the line A—A of FIG. 1A.

As seen in FIGS. 1A and 1B, the electrode array 10 includes a plurality of spaced-apart electrodes 200, formed within a flexible carrier 204. Each of the electrodes is connected to at least one wire 202 which is embedded within the carrier 204. A proximal end of the these wires 202 (not shown) allows selective electrical connection to be made with each electrode 200 to a tissue stimulator, e.g., a cochlear stimulator.

As an important feature of the invention, the electrode array 10 includes a plurality of flexible ribs 14. These flexible ribs 14 help maintain the electrodes 200 in its desired position against the modiolus wall of the cochlea once the electrode array 10 is inserted into the cochlea. In the preferred embodiment, each electrode contact 200 has a corresponding flexible rib 14 located on the opposite side of the electrode array 10 (as shown in FIG. 1A). The ribs 14 can be designed to prevent accidental extraction following initial insertion of the electrode array 10. The rib 14 design does not have to be constant, the ribs 14 can vary in size and shape such that they press against the cochlear wall with varying force along the length of the electrode array 10. In one embodiment, the size of the ribs 14 decrease from the proximal end to the distal end. This design would match the decreasing diameters of the cochlear channel (from the basilar to apical) and allow for a superior fit. In another embodiment, the ribs would have differing stiffness to vary the force that is applied by the rib 14 to the cochlear wall. This can be done by varying the shape and/or thickness of the ribs 14

The electrode array 10 is preferably made from a flexible polymer, and may be molded to assume the curved shape or it may be molded to assume a more straightened shape. While the electrode array 10 may be made in different shapes, a straight shape may allow the electrode array 10 high pushability for insertion through partially ossified cochlear. The straightened shape may also be simpler to manufacture. If curved, the radius of curvature "R" is selected to be approximately equal to, or slightly less than, the natural curvature of the cochlea. That is, when inserted into the cochlea, the electrode array 10 will assume a wind or coil that keeps it near the inner wall of the cochlear channel. This assures that when inserted into the cochlea, the electrodes 200 of the electrode array 10 are positioned near the inner modiolus wall.

Figure 2A:
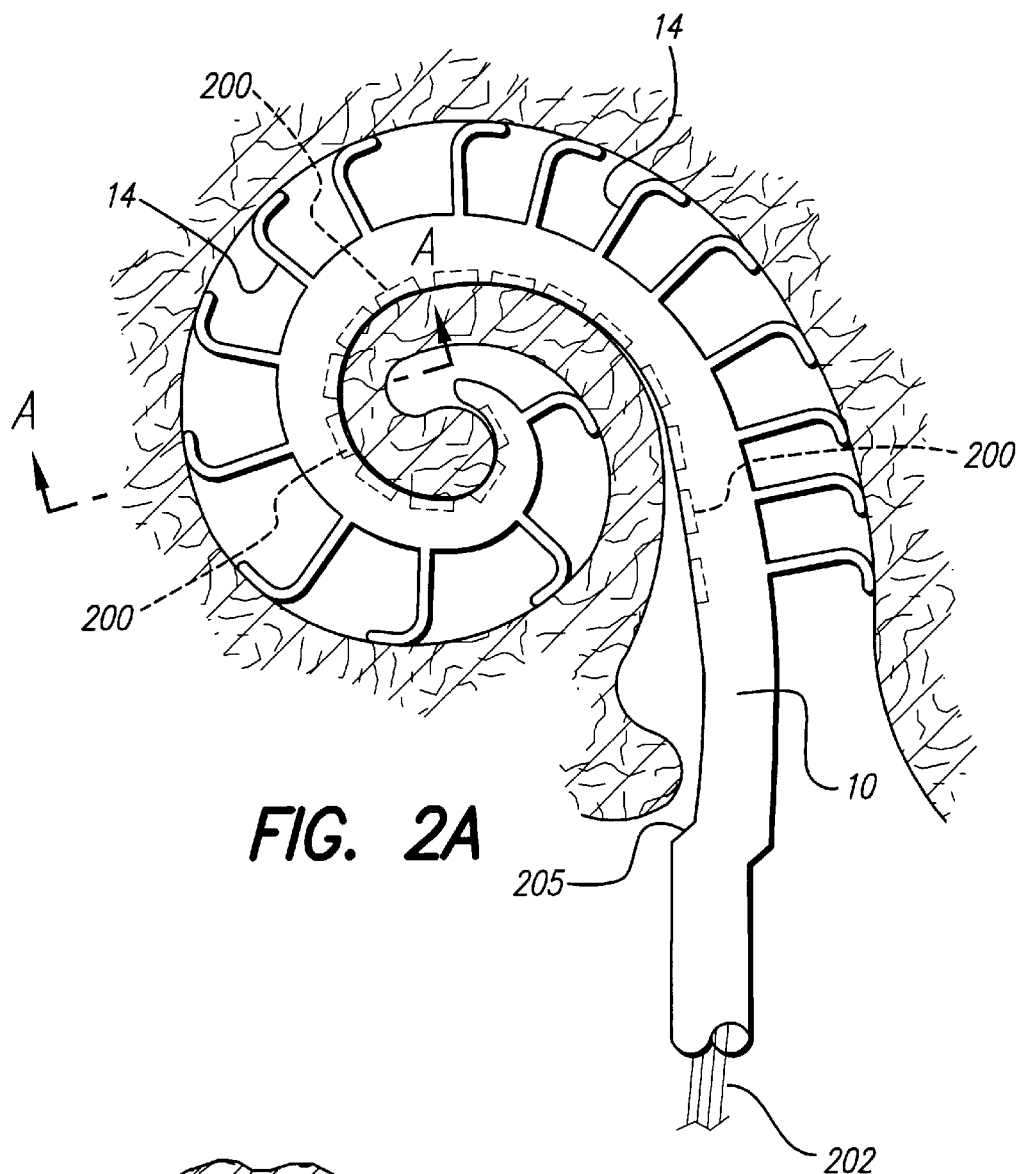
FIG. 2A is a schematic representation of the cochlea showing insertion of the electrode array, and in particular showing the electrode array inserted into the cochlea and showing the flexible ribs positioned against the wall.
Figure 2B:
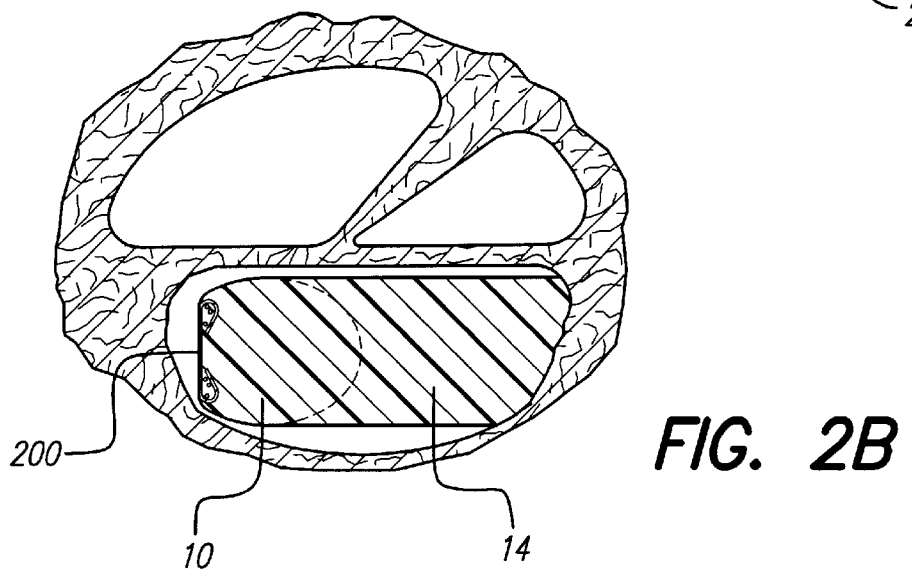
FIG. 2B is a sectional view taken along the line A—A of FIG. 2A.

Next, the method of using the electrode system of the present invention will be described in connection with FIGS. 2A and 2B. First, as shown in FIG. 2A, the electrode array 10 is inserted into the scala tympani (one of the channels of the cochlea) to the desired depth. The desired depth typically involves a rotation of about 360 degrees, as seen best in FIG. 2A. The flexible ribs 14 contact the outer wall of the cochlear channel. As the electrode array 10 is further inserted into the cochlear channel, the flexible ribs 14 force the electrodes 200, which are positioned on the inside curve of the electrode array 10 as it is inserted, into the modiolus wall of the cochlea.

As explained above, the electrode array 10 includes flexible ribs 14 that engage with the outer wall. Once the electrode array 10 has been inserted, the electrodes 200 are positioned very close to the modiolus of the cochlea, as desired. As a final optimization of the position of the electrode contacts 200 of the electrode array 10, the electrode array 10 may be pulled back slightly (about 2 mm). This backward motion assures that the flexible ribs 14 are further engaged with the outer wall, which will force the electrode contacts 200 into direct contact with the modiolus wall.

Some of the advantages of the electrode array 10 is that it may be made thin. The electrode array 10 is thinner than the cochlear channel so that it can be inserted to the apex of the cochlear, and while being inserted, there is room around the electrode array 10 to allow for the expulsion of any liquids present in cochlear channel (as seen in cross-section FIG. 2B).

Turning next to FIGS. 3A through 5, one method of making the electrode array 10 will be described. It is to be emphasize that this method of making the electrode array is not the only way an electrode array suitable for use with the electrode system of the invention could be made. Rather, it merely represents an easy and inexpensive (and thus generally a preferred) way in which the electrode array may be fashioned.

Most designs of electrodes and connectors are based on the principle of molding a contact or array of contacts, usually made from biocompatible metal, into a polymer carrier like epoxy, polyurethane or silicon rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required, e.g., as is the case with a cochlea electrode. The main problem encountered in the fabrication of such electrodes or connectors is to find a reliable method of holding the system of contacts in the desired and stable position during the process of welding the connecting wires and molding the polymer carrier. A further problem relates to maintaining a controlled surface of the contacts that are to remain exposed, i.e., to ensure that the contacts are not covered by the polymer when the carrier is molded.

The preferred method of making the electrode array described below in connection with FIG. 3A through FIG. 5 is based on the principle of attaching (by the process of resistance welding) electrode contacts made from precious, biocompatible material (such as platinum or its alloys) to a foil carrier made from a non-toxic but chemically-active metal like iron (Fe). Attached to the metal carrier, the electrode contacts remain in a desired and stable position allowing easy connecting of the wiring system and subsequent molding of the polymer carrier. After completion of the molding process, the metal foil carrier is etched away using a mixture of diluted acids, such as $HNO_3$ and HCl. The precious metal contacts and polymer are immune to the acid and remain in their intact, unaltered shape, and thereby provide the desired electrode array structure.

Figure 3A:
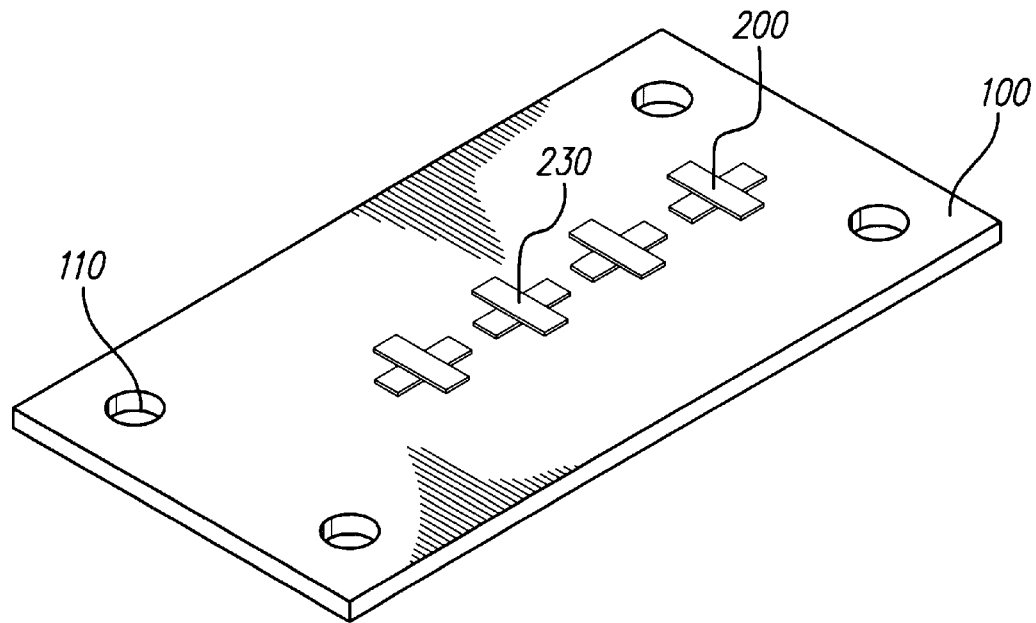
FIG. 3A depicts one manner of making a multi-electrode electrode array of the type shown in FIG. 1A.
Figure 3B:
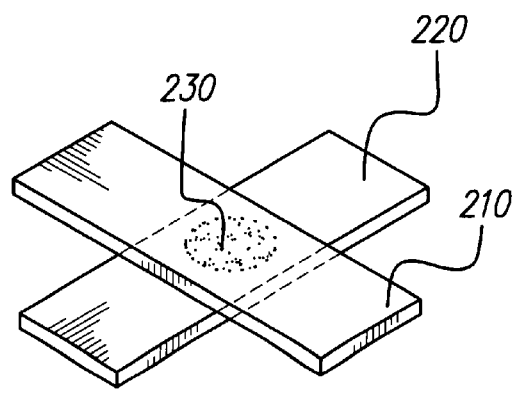
FIG. 3B shows an enlarged view of the electrode contacts of the array of FIG. 1A.

To illustrate this method, the method will be described relative to the fabrication of a multi-electrode electrode array suitable for insertion into the cochlea. As a first step, an array of contacts 200 are welded onto an iron carrier 100 so as to assume a desired spaced-apart relationship, as shown in FIG. 3A. Each contact 200 consists of two pieces of platinum foil 210 and 220, connected together and joined to the carrier 100 by a weld 230, as shown in FIG. 3B.

As a second step, a wiring system is connected to each of the electrode contacts 200. This is accomplished as shown in FIGS. 4A, 4B, 4C and 4D. As seen in FIG. 4B, for example, an insulated wire 202', having the insulation removed from its tip, is laid on top of the electrode foil pieces 210 and 220. One of the ends of the foil piece 220 is then folded over to hold the end of the wire while the wire is welded or crimped in position (FIG. 4B). Then, the other end of the foil 220 is folded over the first folded end (FIG. 4C). If other wires are present, e.g., going to electrode contacts further up the array, then such wires may pass over the foil piece 210, lying parallel to the wire 202' so as to form a bundle of wires 202. A similar bundle may be formed on the other side of the folded foil piece 210, thereby forming another wire bundle 203. The ends of the foil piece 210 may then be folded over the folded piece 220 (FIG. 4D) to complete the wire system connection process.

Figure 5:
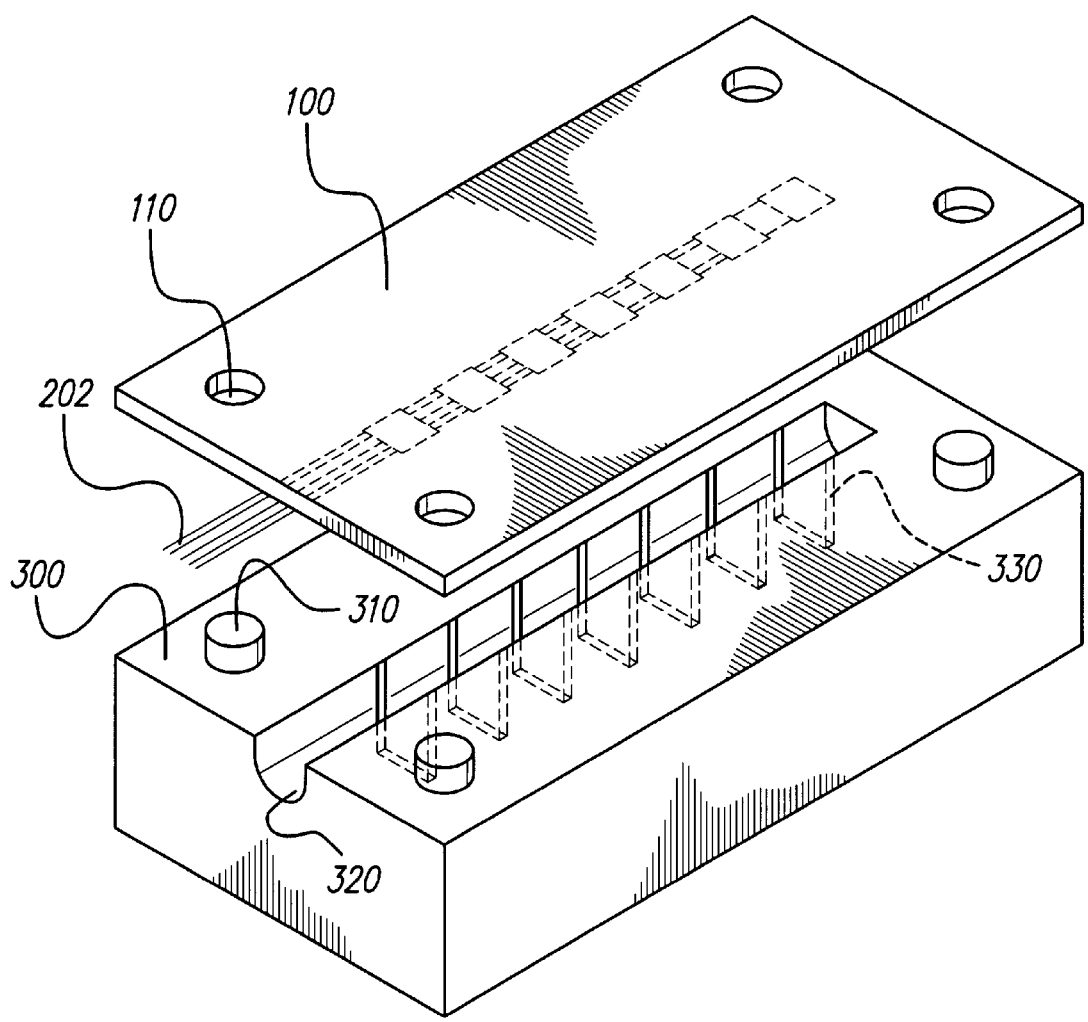
FIG. 5 depicts a molding die onto which the partially-formed electrode array of FIG. 3A, with wires attached to each of the electrodes as shown in FIGS. 4A–4D, may be mounted in order to form a polymer carrier for the electrode array.

Once the wire bundles 202 and 203 have been connected to the electrodes 200, the foil carrier 100 is placed on a molding die 300 as shown in FIG. 5. The die 300 has alignment pegs 310 adapted to align with corresponding alignment holes 110 in the foil carrier 100. The die 300 further has a cavity or channel 320 formed therein into which the required amount of material to form the polymer carrier 204 (FIG. 1A) is injected. This cavity or channel 320 may be shaped or formed as desired, e.g., to include multiple flexible rib cavities 330, or to make the electrode array assume a natural curve shape, or to be straight.

After the material cures, the foil carrier with the electrode array assembly (which is now molded inside of the polymer) is removed from the die 300 and placed in a mixture of diluted acids. The mixture of diluted acids dissolves the foil carrier 100, thereby exposing a clean surface of the electrode contacts 200. After washing to remove any residue of acids and Fe salts, the main electrode array structure is completed.

Alternative Embodiments

Figure 6:
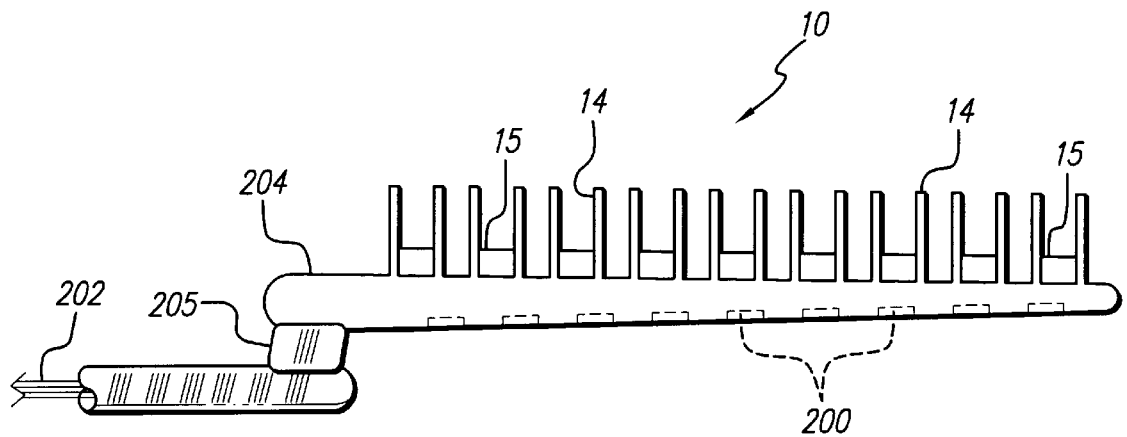
FIG. 6 is a side view of an alternate embodiment of FIG. 1 showing the stiffening members positioned between the flexible ribs.

The shape, size and location of the flexible ribs 14 relative to the electrodes 200 and position of each rib 14 should be selected such that the ribs 14 optimize the performance of the entire electrode array 10. The function of the rib 14 could be enhanced by adding stiffening members 15 in strategic locations on the back side of the electrode array 10. The stiffening members 15 are positioned longitudinally along the rear side of the electrode array 10 and may be continuous (between all of the flexible ribs 14) or between selected flexible ribs 14. FIG. 6 shows an embodiment of the present invention where the stiffening members 15 are located between the flexible ribs 14, opposite each electrode 200. The stiffening members 15 may prevent buckling of the electrode array 10 in the area of the electrode 200.

Figure 7:
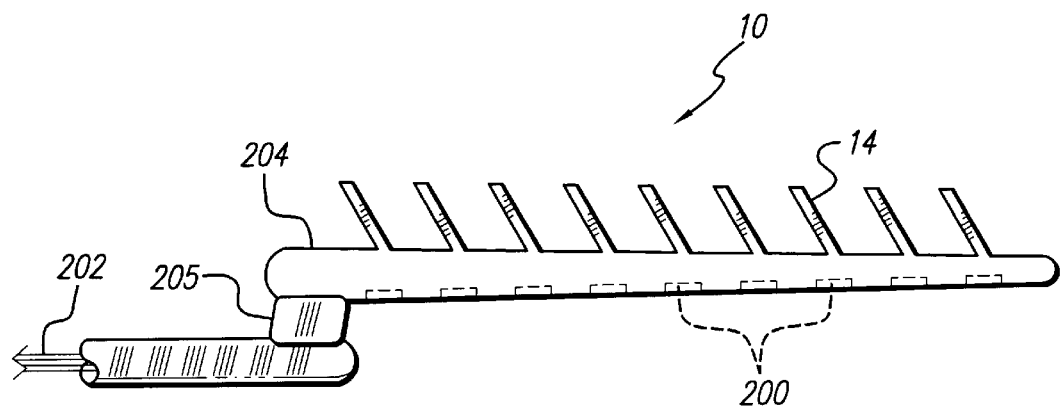
FIG. 7 is a side view of an alternate embodiment of FIG. 1 showing angled flexible ribs.

FIG. 7 shows another embodiment for the ribs 14. In this case, the ribs (which may also be called fins) 14 are angled proximally (i.e., backwards toward the end of the electrode array 10) and the size of the ribs 14 decrease from the proximal end to the distal end. This design would match the decreasing diameters of the cochlear channel (from the basilar to apical) and allow for a superior fit. As described above, it is thus seen that an electrode system is provided wherein engagement of the flexible ribs 14 against the cochlear walls, stabilizes the electrode contacts 200 in the desired and optimal position in direct contact with the modiolus wall.

Note, typically the electrode array 10, as seen best in FIG. 1A, has an offset 205 on the same side as the electrodes 200. Such offset 205 functions as a stop to prevent the electrode array 10 from being inserted too deep into the cochlea. Even when such offset cannot effectively function as a stop, it can always function as a mark, to aid the physician to know when the desired insertion depth has been achieved. The offset 205 may also be located opposite the electrodes 200, on the same side as the ribs 14 and add directionality of the electrode during the insertion into the cochlear channel.

While the invention herein disclosed has been described by means of specific embodiments and applications thereof, numerous modifications and variations could be made thereto by those skilled in the art without departing from the scope of the invention set forth in the claims.

What is claimed is:

1. An electrode system adapted for use with a tissue stimulation device comprising:
    a flexible electrode array having front and rear sides adapted for insertion into a body cavity having outer and inner walls;
    a multiplicity of electrode contacts along the front side of the electrode array;
    means for electrical connection between the electrode contacts and the tissue stimulation device; and
    a plurality of flexible ribs positioned along the rear side of the electrode array opposite the electrode contacts;
    wherein the flexible electrode array is insertable into the body cavity such that the flexible ribs contact the outer wall of the body cavity and the electrode contacts are adjacent to the inner wall of the body cavity.

2. The electrode system as set forth in claim 1 wherein the body cavity comprises the scala tympani of a human cochlea, and wherein the electrode system comprises part of a cochlear stimulation system.

3. The electrode system as set forth in claim 1 wherein the flexible ribs are curved toward a proximal end of the electrode array such that once the electrode array is inserted into the body cavity, the flexible ribs interface with the outer wall of the body cavity securing the electrode array in its desired position with the electrode contacts held against the inner wall of the body cavity.

4. The electrode system as set forth in claim 1 wherein the flexible ribs increase in size from a distal end to a proximal end of the electrode array.

5. The electrode system as set forth in claim 1 wherein each electrode contact on the front side of the electrode array has a corresponding flexible rib on the rear side.

6. The electrode system as set forth in claim 1 wherein each electrode contact on the front side of the electrode array has a corresponding stiffening member between a pair of flexible ribs located on the rear side.

7. The electrode system as set forth in claim 1 wherein the means for electrical connection between the electrode contacts and the tissue stimulation device comprises a bundle of insulated wires, each electrode contact having a corresponding insulated wire.

8. The electrode system as set forth in claim 7 wherein the bundle of insulated wires are molded into the flexible electrode array.

9. A cochlear electrode array for insertion into the scala tympani of a human cochlea, one side or wall of the scala tympani comprising a modiolar wall, said electrode array comprising:
    a flexible body portion;
    a plurality of spaced-apart electrode contacts exposed near a front side of the body portion;
    a plurality of wires embedded within the body portion, at least one wire of the plurality of wires making electrical contact with one of the plurality of electrode contacts; and
    a plurality of ribs extending from a back side of the body portion, said ribs having a size that causes an edge of the rib to contact a wall of the scala tympani opposite the modiolar wall, whereby the electrode contacts are positioned near the modiolar wall.

10. The cochlear electrode array as set forth in claim 9 wherein the flexible ribs increase in size from a distal end to a proximal end of the electrode array.

11. The cochlear electrode array as set forth in claim 9 wherein each electrode contact exposed near the front side of the body portion has a corresponding flexible rib on the back side of the body portion.

12. The cochlear electrode array as set forth in claim 9 wherein each electrode contact exposed near a the front side of the body portion has a corresponding stiffening member between a pair of flexible ribs located on the back side of the body portion.

13. A method of inserting an electrode array into a cochlea, the electrode array having a multiplicity of spaced-apart electrode contacts along a front edge thereof and further having a plurality of flexible ribs protruding from a back edge thereof, the method comprising:

inserting the electrode array into one of the channels of the cochlea to a desired depth, which desired depth typically comprises a rotation of at least 360 degrees and causes the plurality of flexible ribs located on the back side of the electrode array to contact an outer or lateral wall of the channel wherein it is inserted, the flexible ribs positioning the multiplicity of spaced-apart electrode contacts located along the front side of the electrode array into a position adjacent a inner wall of the body cavity.

14. The method of claim 13 wherein the electrode array with flexible ribs is larger in cross-sectional area than the cochlear channel such that when the flexible ribs contact the outer wall during insertion, the flexible ribs are flexed toward a proximal end of the electrode array, urging the electrode contacts against the inner wall of the cochlear channel.

15. The method of claim 14 further including the step of pulling back on the electrode array slightly such that the flexible ribs further engage the outer wall of the cochlear channel, locking the electrode array in a desired position within the cochlear channel.

* * * * *